United States Patent [19]

Robinson et al.

[11] 4,152,210

[45] May 1, 1979

[54] BIOLOGICALLY ACTIVE MATERIALS ATTACHED TO A FERROMAGNETIC SUPPORT

[75] Inventors: Peter J. Robinson; Peter Dunnill, both of London; Malcolm D. Lilly, Orpington, all of England

[73] Assignee: Beecham Group Limited, Brentford, England

[21] Appl. No.: 573,306

[22] Filed: Apr. 30, 1975

Related U.S. Application Data

[63] Continuation of Ser. No. 281,655, Aug. 18, 1972, abandoned.

[30] Foreign Application Priority Data

Aug. 27, 1971 [GB] United Kingdom ............... 40297/71

[51] Int. Cl.$^2$ ................................................ C07G 7/02
[52] U.S. Cl. ........................................ 195/63; 195/68; 195/DIG. 11; 195/116

[58] Field of Search ................... 195/63, 68, DIG. 11, 195/116; 210/222

[56] References Cited

U.S. PATENT DOCUMENTS

| | | | |
|---|---|---|---|
| 3,351,203 | 11/1967 | Robb ............................... | 210/222 X |
| 3,470,067 | 9/1969 | Warren et al. .................. | 210/222 X |
| 3,519,538 | 7/1970 | Messing et al. ........................ | 195/63 |
| 3,705,084 | 12/1972 | Reynolds ............................... | 195/63 |
| 3,796,634 | 3/1974 | Haynes et al. ........................ | 195/63 |

*Primary Examiner*—David M. Naff
*Attorney, Agent, or Firm*—Finnegan, Henderson, Farabow & Garrett

[57] ABSTRACT

Biologically active materials such as enzymes attached to a ferromagnetic support such as iron or iron oxide particles enable a magnetic separation of the supported biologically active material from a reaction medium after carrying out a biochemical reaction.

19 Claims, No Drawings

BIOLOGICALLY ACTIVE MATERIALS ATTACHED TO A FERROMAGNETIC SUPPORT

This is a continuation, of application Ser. No. 281,655, filed Aug. 18, 1972, said application now abandoned.

This invention relates to a process for carrying out biochemical reactions using a biologically active organic material attached to a solid support.

The utility of enzymes as catalysts and other biologically active organic materials such as, for example, antigens, antibodies and co-factors in biochemical reactions, can be increased by attaching them to solid supports so that, for example, they can be removed from the reaction mixture or used in processes in which the reactants flow continuously over them. Furthermore, the stability of a biologically active organic material attached to a solid support is often greater than that of the same material in the free state. However a major drawback which has been encountered in practice is that it is often required to carry out biochemical reactions using reaction media which are viscous or which contain suspended solid materials. Viscous media make it difficult to separate the solid support from the reactants, and suspended solids have a tendency to deposit on the solid support, particularly in continuously operated biochemical processes using packed beds of the support material, thus reducing the activity of the biologically active organic material and necessitating frequent cleaning of the support. Hitherto the solid supports which have been used are usually polymeric organic materials having a density comparable to that of the suspended solids, thus increasing the difficulty of separation.

In the present invention the biologically active organic material is attached to a solid ferromagnetic support, thus enabling a magnetic separation of the support from the deposited suspended solids to be carried out.

According to the present invention there is provided a process for carrying out a biochemical reaction in which a biologically active organic material attached to a solid ferromagnetic support is contacted with a reaction medium, which comprises the step of magnetising the support and thereby effecting a separation of the biologically active material from the reaction medium.

The process may be carried out batch-wise or continuously. In batch operation the separation may be effected by applying a magnetic field to the reaction medium after reaction and removing the reaction medium whilst retaining the magnetised support carrying the biologically active organic material in the magnetic field. In a continuous process the ferromagnetic support with the biologically active organic material attached thereto may, for example, be contained within a reactor by a magnetic field and the reaction medium flowed continuously through the reactor.

A wide range of biologically active organic materials can be used in the process of the present invention including enzymes present in or isolated from animal, plant or microbiological tissue such as, for example, proteolytic enzymes such as trypsin, chrymotrypsin and papain; hydrolases such as β-galactosidase, ribonuclease, alkaline phosphatase, amyloglucosidase and dextranase; dehydrogenases such as lactic dehydrogenase; kinases such as creatine phosphokinase, and pyruvate kinase; oxidases such as glucose oxidase; and amidases such as amidase and penicillin amidase. Alternatively, the biologically active organic material may be a co-factor such as, for example, nicotinamide adenine dinucleotide (NAD), nicotinamide adenine dinucleotide phosphate (NADP) and their reduced forms, adenosine diphosphate ribose (ADP-Ribose), adenosine triphosphate (ATP), adenosine diphosphate (ADP), adenosine monophosphate (AMP), pyridoxamine phosphate, pyridoxal phosphate, a pterin, a flavin, or co-enzyme A; an inhibitor such as, for example an organophosphorus compound; or an antigen or antibody.

The ferromagnetic support may for example comprise metals such as iron, cobalt or nickel, or alloys thereof. The use of metal oxides is often preferred as these are less subject to corrosion. Particularly useful ferromagnetic materials include iron, iron oxide, steels and various ferrites such as strontium ferrite. In a particularly preferred embodiment of the invention the support is used in particulate form and, for example, particles having a diameter of from 5 to 1000 microns, especially from 10 to 100 microns have been found to be highly advantageous. Other suitable shapes for example rings, rods or cylinders which nevertheless enable the support to be separated from the deposited suspended solids by magnetic means may however be used as convenient. The surface of the ferromagnetic support may be porous to increase the available surface area.

The biologically active organic material may be attached to the ferromagnetic support using a variety of methods. However the biologically active organic material is preferably attached to an organic polymeric material which is itself attached to the ferromagnetic support. For example, the support may be formed into a composite material with, or coated with a film of, an organic polymeric material such as for example nylon, polyurethane or a cellulose derivative such as α-cellulose and the biologically active organic material attached to the polymeric material chemically, that is to say by the formation of a covalent bond involving groups not essential to the activity of the organic material, by adsorption, or by entrapping the biologically active organic material between the interstices of the polymer. Suitable methods for chemically attaching biologically active organic materials to polymeric materials are described in British Patent Nos. 1,183,257 and 1,183,259. Other attachment methods include the formation of azide groups, or bromocetyl groups, on the polymer which can react with the biologically active organic material. In an alternative procedure the ferromagnetic support having a surface layer of oxide is chemically attached to the biologically active organic material by the use of certain silanes, such as 3-aminopropyltriethoxysilane. A suitable method for carrying out this reaction is described in Biochimica Et Biophysica Acta 206(1970)54–60.

The ferromagnetic support having the biologically active organic meterial attached thereto may be recovered from the reaction medium for re-use, or contained within a reactor without the necessity for a physical barrier, by the appropriate application of a magnetic field. The particles may, for example, be contained magnetically within a reactor in the form of fluidised bed. In a further embodiment magnetised particles of the ferromagnetic support carrying the biologically active organic material may be dispersed in the reaction medium in a stirred reactor. After reaction, stirring is discontinued and the magnetised particles allowed to flocculate and settle. The tendency for the magnetised particles to flocculate greatly reduces the settling time in comparison with similar particles in an unmagnetised state, and thus permits their ready removal from the base of the reactor. It has been found that in a stirred reactor reaction rates are substantially unaffected by magnetisation of the support.

The magnetic field may be provided by a permanent magnet or an electromagnet, and may be applied intermittently or continuously. An electromagnet may be used to generate an alternating magnetic field which can have the further advantage when a particulate support is used of causing micro-mixing of the particles with the reaction medium.

The insoluble biologically active organic materials of the invention can be used in a wide variety of biochemical reactions, and are often suitable for use in processes in which soluble biologically active organic materials have previously been used. Thus they may, for example, be used in the preparation of penicillins, beer clarification, the preparation of glucose using amyloglucosidase, the preparation of optically active amino acids, and the formation of L-alanine by transamination. Other potential uses include acid hydrolysis of cabohydrates, the processing of waste materials, the specific manipulation of large natural molecules such as steroids, alkaloids, chloramphenicol and riboflavine, alcoholic and other kinds of fermentation, the fixing of nitrogen, a luciferase system for ATP estimation, biochemical fuel-cells, and the specific oxidation and reduction of organic materials including carbon dioxide fixation.

The invention is illustrated by the following Examples:

EXAMPLE 1

20 g nickel plated iron beads (approx. 30 to 80 mesh) are mixed with excess 2% solution in acetone of 3-aminopropyltriethoxysilane. Excess liquid is removed and the beads are allowed to incubate at 45° C. for 24 hours. The beads are then suspended in 100 ml of cold 1% aqueous glutaraldehyde for 30 minutes. The liquid is decanted off and the beads are washed with cold 1% $KHCO_3$ solution, pH 8.2. Cold 20 ml of chymotrypsin solution (4 mg/ml in 1% $KHCO_3$, pH 8.2) is added to the beads, and the pH is adjusted to 7.5 with dilute HCl. After two hours the liquid is decanted off and the beads are washed with 0.2 M bicarbonate buffer, pH 7.5. The preparation is used in a stirred tank to hydrolyse acetyl-L-tyrosine ethyl ester ($2\times10^{-2}$M, in 0.1 M-NaCl solution). The activity of the preparation at 25° C. is 35$\mu$ moles/min/g support. The preparation is quantitatively recovered from the solution using a permanent magnet and used immediately to hydrolyse a further batch of substrate. No loss in activity is detected.

EXAMPLE 2

This Example describes the preparation of an enzyme attached to a solid support comprising iron oxide particles.

25 g of precipitated $Fe_3O_4$ is dried at 200° C. for 20 hours. The powder is then refluxed for 12 hours in 200 ml of a 2% solution of 3-aminopropyltriethoxysilane in toluene. After reflux the powder is washed by decantation, twice with 200 ml of toluene and once with acetone. The powder is then dried in an oven at 45° C.

Two separate 1 gram portions of the powder are washed three times with water and precipitated each time using a large permanent magnet. To each portion 20 ml of cold distilled water containing 2% glutaraldehyde are added and stirred mechanically for 30 minutes. After this period the glutaraldehyde is removed by a single rinse in cold 0.1 M phosphate buffer, pH 7.0. Each portion then receives 10 ml of a 5 mg/ml protein solution, in 0.1 M phosphate, pH 7.0, in one case the solution containing $\beta$-galactosidase of specific activity 110 units/mg, and in the other chymotrypsin of specific activity 265 units/mg.

After 3 hours stirring at 4° to 10° C. the chymotrypsin derivative is washed by magnetic decantation with the above phosphate buffer. The $\beta$-galactosidase derivative is washed in similar fashion, but 0.1 M 2-mercaptoethanol is added to the buffer.

The activity of the $\beta$-galactosidase derivative, measured at 37° C. is 1825 units per gram dry weight, and that of the chymotrypsin derivative measured at 23° C. is 800 units per gram dry weight.

The chymotrypsin derivative (30 milligrams dry weight) is used in a stirred tank (Lilly and Sharpe "The Chemical Engineer" 215 Jan./Feb. 1968) to hydrolyse 78 milligrams of acetyl-L-tyrosine ethyl ester in 600 ml of 0.2 M salt solution. The activity of the enzyme derivative is determined at different stirrer speeds. The enzyme derivative is collected between runs by applying a permanent magnet to the base of the tank whereupon the majority of the particles of the enzyme derivative sink to the bottom. The remaining fine particles may be removed from the reaction medium by allowing the reaction medium to flow through a small channel to which a magnetic field is applied.

| Stirrer speeds (rpm) | Activity ($\mu$ moles/min.) |
| --- | --- |
| 120 | 17.9 |
| 200 | 17.5 |
| 300 | 17.9 |
| 400 | 18.1 |
| 500 | 18.6 |
| 600 | 18.7 |

EXAMPLE 3

This Example describes the attachment of an enzyme to a composite iron oxide/polymer material.

50 g of Whatman CF2 cellulose is mercerised with 15% NaOH at 50° C. for 2 hours. The suspension is filtered and washed. The product is 38 g of $\alpha$-cellulose.

Freshly precipitated $Cu(OH)_2$ is dried on a filter paper and added in excess to fresh ammonia solution. The resulting dark-blue liquid is filtered on a glass filter paper and the filtrate cooled on ice.

$\alpha$-cellulose powder is stirred into 25 ml of the cold cuprammonium hydroxide solution until the solution becomes noticeably viscous. The liquid at this stage is clear, denoting that the cellulose has completely dissolved. This process takes approximately 30 minutes.

30 g of $Fe_3O_4$ is stirred into the solution and stirring continued for 15 minutes to ensure mixing. The viscous slurry is extruded under pressure through a 2 mm nozzle into 0.2 N HCl and allowed to stand for 30 minutes. The thread is then washed with water and dried.

After grinding the powder is identical in appearance to the original $Fe_3O_4$ powder but contains 20 to 30% $\alpha$-cellulose.

1 g of the magnetic cellulose is activated with 200 mg of cyanogen bromide by automatic titration at pH 11.0 (Axen, Porath and Emback, Nature 1967 214 page 1302). The material is washed by precipitation using a magnet and subsequent decantation.

The washed derivative is suspended in 20 ml of a 5 mg/ml solution of $\beta$-galactosidase (specific activity 110 units/mg) in 0.1 M phosphate buffer, pH 8.5, and stirred for 20 hours at 4° C. The magnetic enzyme derivative is washed with 0.1 M phosphate buffer, pH 8.5 containing 0.01 M 2 mercaptoethanol.

The activity of the β-galactosidase derivative is measured by stirring with a solution of o-nitrophenol galactoside in 0.1 M phosphate buffer pH 7 and the production of o-nitrophenol subsequently measured by absorption at 420 nm. The activity at 37° C. is found to be 895 units per gram dry weight. After reaction the β-galactosidase derivative is collected by magnetic precipitation as described in Example 2.

A chymotrypsin derivative is prepared in a similar manner to the β-galactosidase derivative except that the mercaptoethanol is omitted from the phosphate buffer. The activity of this derivative is found to be 306 units per gram dry weight.

We claim:

1. A biochemically reactive substance which comprises an enzyme attached to a solid iron or iron oxide ferromagnetic support in particulate form with the support particles having a particle diameter of from 5 to 1000 microns.

2. A biochemically reactive substance according to claim 1 in which the particles have a diameter of from 10 to 100 microns.

3. A biochemically reactive substance according to claim 1 in which the enzyme is attached to an organic polymeric material which is itself attached to the ferromagnetic support.

4. A biochemically reactive substance according to claim 3 in which the support is formed into a composite material with an organic polymeric material and the enzyme is attached to the polymeric material.

5. A biochemically reactive substance according to claim 3 in which the support is coated with a film of an organic polymeric material and the enzyme is attached to the organic polymeric material.

6. A biochemically reactive substance according to claim 3 in which the enzyme is chemically attached to the organic polymeric material.

7. A biochemically reactive substance according to claim 1 in which the ferromagnetic support having a surface layer of oxide is chemically attached to the enzyme by the use of 3-aminopropyltriethoxysilane.

8. A process for carrying out a biochemical reaction comprising the steps of:
    (a) contacting an enzyme attached to a particulate iron or iron oxide ferromagnetic support, with the support particles having a particle diameter of from 5 to 1000 microns, with a reaction medium in a reaction vessel to effect a biochemical reaction;
    (b) applying a magnetic field to the reaction medium and the enzyme attached to the particulate ferromagnetic support sufficient to retain the enzyme within the reaction vessel; and
    (c) removing the reaction medium after the reaction is completed from the reaction vessel, thereby effecting a separation of the enzyme from the reaction medium.

9. A process according to claim 8 in which the particles have a diameter of from 10 to 100 microns.

10. A process according to claim 8 in which the enzyme is attached to an organic polymeric material which is itself attached to the ferromagnetic support.

11. A process according to claim 10 in which the support is formed into a composite material with the organic polymeric material and the enzyme is attached to the polymeric material.

12. A process according to claim 10 in which the support is coated with a film of the organic polymeric material and the enzyme is attached to the organic polymeric material.

13. A process according to claim 10 in which the enzyme is chemically attached to the organic polymeric material.

14. A process according to claim 8 in which the ferromagnetic support having a surface layer of oxide is chemically attached to the enzyme by the use of 3-aminopropyltriethoxysilane.

15. A process according to claim 8 in which the support is a particulate support which is magnetised by the use of an alternating magnetic field.

16. A process according to claim 8 in which the magnetic field is applied in step (b) after the reaction has been completed.

17. A process according to claim 8 in which the reaction medium is continuously flowed through the reaction vessel and the magnetic field is applied throughout the reaction so as to retain the enzyme in the reaction vessel.

18. A process for carrying out a biochemical reaction comprising the steps of:
    (a) contacting an enzyme attached to a particulate iron or iron oxide ferromagnetic support, with the support particles having a particle diameter of from 5 to 1000 microns, with a reaction medium to form a reaction mixture in a reaction vessel to effect a biochemical reaction;
    (b) applying a magnetic field to the reaction mixture and stirring the reaction mixture;
    (c) discontinuing stirring of the reaction mixture after the reaction has been completed, but retaining the magnetic field while allowing the magnetized particles to flocculate and settle to the bottom of the reaction vessel; and
    (d) removing the enzyme from the bottom of the reaction vessel thereby effecting a separation of the enzyme from the reaction medium.

19. A process according to claim 18 in which the bottom of the reaction vessel is magnetized.

* * * * *